| United States Patent [19] | [11] Patent Number: 5,073,490 |
|---|---|
| Babinet et al. | [45] Date of Patent: Dec. 17, 1991 |

[54] TRANSHYBRIDOMAS

[75] Inventors: Charles Babinet; Dominique Morello, both of Paris, France

[73] Assignee: Institut Pasteur, Paris, France

[21] Appl. No.: 488,479

[22] Filed: Feb. 27, 1990

Related U.S. Application Data

[63] Continuation of Ser. No. 863,156, May 14, 1986, abandoned.

[30] Foreign Application Priority Data

Mar. 28, 1986 [FR] France ............................ 86 04556

[51] Int. Cl.$^5$ .................... C12N 5/00; C12N 15/00
[52] U.S. Cl. .......................... 435/240.2; 435/240.26; 435/69.4; 435/172.2; 435/172.3; 800/2; 800/DIG. 1; 935/70; 935/103
[58] Field of Search .................. 800/2, DIG. 1; 435/69.1, 69.4, 172.3, 240.2, 240.26, 172.2, 317.1; 935/89, 93, 95, 103, 104

[56] References Cited

U.S. PATENT DOCUMENTS

| 4,332,893 | 6/1982 | Rosenberg | 435/68 |
|---|---|---|---|
| 4,621,053 | 11/1986 | Sugimoto | 435/68 |
| 4,736,866 | 4/1988 | Leder et al. | 800/1 |

FOREIGN PATENT DOCUMENTS

| 0089666 | 3/1983 | European Pat. Off. |
|---|---|---|
| 84/02534 | 12/1983 | PCT Int'l Appl. |
| 2092158 | 12/1981 | United Kingdom |

OTHER PUBLICATIONS

Palmiter et al., Science 222: 809–814 (1983).
Low et al., Science 231: 1001 1004 (1986).
Köhler et al., Nature 256: 495–497 (1975).
Steinitz et al., Nature 269: 420–422 (1977).
Tooze, "The Molecular Biology of Tumor Viruses", pp. 99–100 and 490–491, Cold Spring Harbor Laboratory (1973).
Brinster et al., Nature 306: 332–336 (1983).
Ritchie et al., Nature 321: 517–520 (1984).
Ornitz et al., Nature 313: 600–602 (1985).
Lichtman et al., Nature 324: 489–491 (1986).

*Primary Examiner*—Elizabeth C. Weimar
*Assistant Examiner*—Jasemine C. Chambers
*Attorney, Agent, or Firm*—Finnegan, Henderson, Farabow, Garrett & Dunner

[57] ABSTRACT

Tissue cell culture preparations derived from the cells of a transgenic animal are disclosed. These tissue cell preparations are capable of expressing a non-analogous gene product, i.e., a gene product which is not naturally produced by the animal cells.

Transhybridomas, i.e., hybridomas and immortalized cells created using cells obtained from transgenic animals, and methods for creating these transhybridomas are also disclosed. In particular, two transhybridomas, A 15.9 and B 6.4, both capable of producing human growth hormone, have been disclosed.

2 Claims, 1 Drawing Sheet

TRANSHYBRIDOMAS

This application is a continuation of application Ser. No. 06/863,156 filed May 14, 1986, now abandoned.

BACKGROUND OF THE INVENTION

Production of proteins of biological interest has been, in recent years, a primary goal of the genetic engineering field. The present inventors have developed a method for producing such proteins through the use of "transhybridomas," i.e., hybridomas produced using lymphocytes of transgenic animals.

The ability to introduce foreign genes into mammalian embryos has been recently developed. This method for the creation of so-called "transgenic" animals has allowed increased study of gene regulation and the genetic basis for development. To develop a transgenic animal, foreign DNA is introduced into the mammalian genome by micro-injection of DNA molecules into the pronuclei of fertilized eggs. The fertilized eggs are then inserted into the reproductive tracts of foster mothers and continue to develop there, eventually resulting in the birth of the transgenic animals. Because integration of the foreign DNA into the mammalian chromosome occurs at an early stage in embryo development, there is ubiquitous transfer of the foreign DNA throughout the germ line.

Various researchers have described the basic process for the creation of transgenic animals, particularly mice. For example, Palmiter et al., in "Dramatic Growth of Mice That Develop From Eggs Microinjected with Metallothionein-Growth Hormone Fusion Genes," Nature. Vol. 300, 611–615 (Dec. 1982). Alt et al., have summarized some features of immunoglobulin genes in transgenic mice In Trends In Genetics, Aug., 1985, pp. 231–236. Both of these papers, which are specifically incorporated herein by reference, describe these processes.

As indicated by the title of the article, Palmiter et al. discloses the integration of a metallothionein-rat growth hormone fusion gene into the mouse genome, observing rapid growth of the resultant transgenic mice. On the other hand, Alt et al. reported the production of a transgenic mouse expressing a mouse immunoglobulin transgene from the lymphocytes. In addition, lymphocytes, described by Ritchie et al. in Nature 312:517 (1986), have been made to synthesize murine immunoglobulins. However, these lymphocytes are cells which would normally synthesize the corresponding mouse immunoglobulins. Thus, to date, there have been no published reports in the literature of the in vitro expression, using cells obtained from transgenic animals, of gene products of human genes wherein the transgenic animal cell does not normally express an analogous animal gene product.

The present inventors, however, have succeeded in obtaining consistent, high levels of expression of human growth hormone, normally produced by pituitary cells, from transgenic mouse lymphocytes. In addition, the present inventors have developed a technique for the creation of certain hybridomas, hereinafter referred to as "transhybridomas." This method involves the fusion of a transgenic animal cell, which is producing a foreign gene product not analogous to a gene product normally produced by that cell, with an immortal cell line.

Using the method of the present invention and the transhybridoma that this method creates, it may be that large quantities of foreign gene products, especially proteins, can be obtained. In addition, through the use of a signal peptide, gene products which are not normally secreted from a cell may be produced and secreted from these transhybridomas, resulting in commercially-applicable processes and products for the production of useful proteins.

SUMMARY OF THE INVENTION

One object of the present invention is to provide transgenic mammalian cells which are capable of expressing the gene product of a foreign gene, when the cell would not normally express the analogous native gene product. In addition, it is an object of the present invention to create hybridomas from these transgenic animal cells, which hybridomas are capable of producing, preferably in commercially-useful quantities, the gene products expressed by the transgenic animal cells. In particular, it is also an object of the present invention to provide specific transhybridomas which meet the foregoing requirements and which have been created through the methods described herein.

Additional objects and advantages of the invention will be set forth in part in the description that follows or may be learned from practice of the invention. The objects and advantages may be realized and attained by means of the instrumentalities and combinations particularly pointed out in the appended claims.

To achieve the objects and in accordance with the purposes of the present invention, preparations of various transgenic animal cells are disclosed which are capable of synthesizing foreign gene products which are not analogous to those native gene products normally produced by the cells. Using these transgenic cells, a method for the production of transhybridomas is then described. These transhybridomas, in addition to being immortal, are capable of synthesizing the gene products produced by the transgenic cells. Generally, the method for the creation of these transhybridomas and producing gene products includes:

(a) selecting a host animal from which a fertilized egg can be obtained;

(b) selecting a particular cell type of the host animal, which cell type is capable of being fused with an immortal cell line or otherwise capable of being immortalized;

(c) constructing a fusion gene comprising promoter-/enhancer elements competent in the selected host animal cell type and the DNA sequences encoding a desired gene product to be produced;

(d) introducing the fusion gene into the host animal genome by micro-injection of the fusion gene into the pro-nucleus of a fertilized host animal egg;

(e) allowing the fertilized host animal egg containing the fusion gene to develop into a transgenic version of the host animal;

(f) segregating the now-transgenic selected cells of the animal host which are producing the gene product from the transgenic animal;

(g) fusing the now-transgenic selected cells to cells obtained from an immortal cell line to create a transhybridoma or otherwise causing the cells to become immortalized;

(h) culturing the transhybridoma; and (i) harvesting the gene product from the transhybridoma.

The fusion genes referred to herein may be either synthetic DNA sequences or restriction fragments, i.e., DNA sequences of excised from larger, naturallyoccurring DNA sequences. In a preferred embodiment, the fusion gene in part encodes a protein known as human growth hormone ("hGH").

It is to be understood that both the foregoing general description and the following detailed description are exemplary and explanatory only and are not restrictive of the invention, as claimed. The accompanying drawings, which are incorporated in and constitute a part of this specification, illustrate various embodiments of the invention, and, together with the description, serve to explain the principles of the invention.

DETAILED DESCRIPTION OF THE PREFERRED EMBODIMENTS

Figure 1:
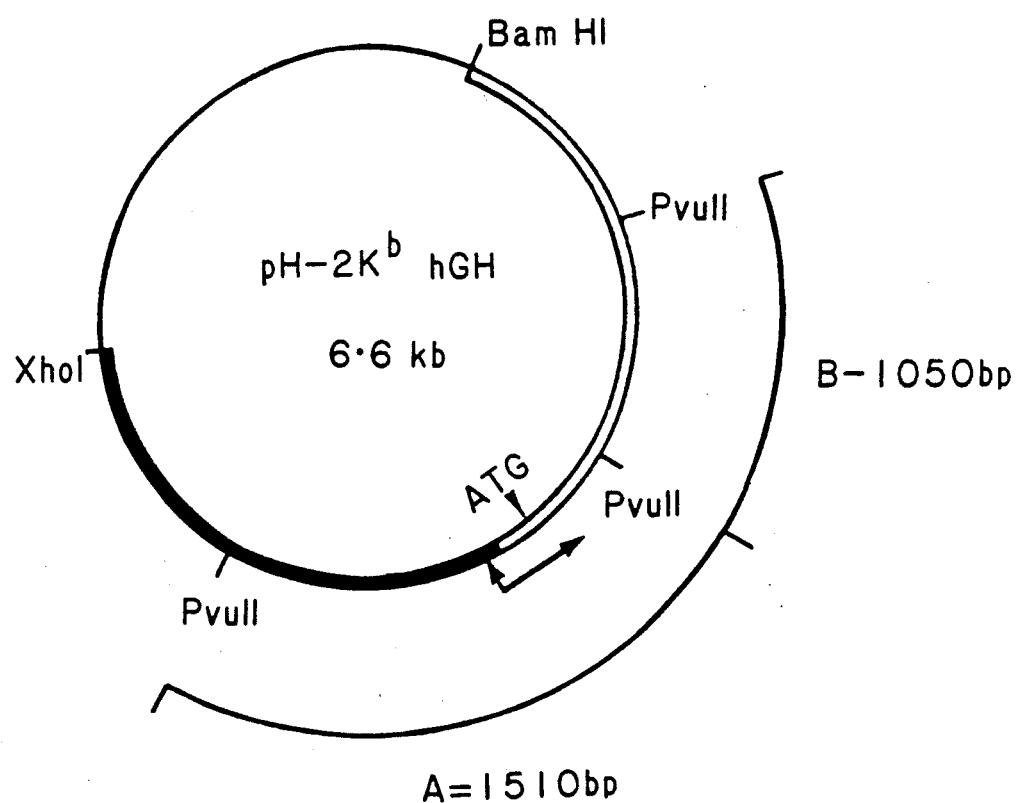
FIG. 1 is a restriction map of plasmid pH-2K$^b$hGH.

The present invention relates generally to the production of transhybridomas, using transgenic animal cells and immortal cell lines. The following detailed description uses, by way of example, a description of the invention in which transgenic animal lymphocyte cells and human growth hormone (hGH) genes are referenced. The use of lymphocyte cells and of hGH genes in the ensuing discussion should be viewed as illustrative of the invention disclosed herein in its broader respects and defined in the claims which follow and not as a limitation on the intended scope of those claims.

As noted above, this specification describes preparation of cells from transgenic animals which are capable of producing nonanaloguous gene products, which gene products are not analogous to proteins normally produced by the animal cells. In addition, the specification describes methods for the creation of transhybridomas using, in one embodiment, these transgenic animal cells and in another embodiment a transgenic animal cell producing any useful gene product. Specific transhybridomas created by this method are also disclosed.

As the term is used herein, the "non-analogous gene product" produced by the transgenic host animal cell is a gene product, generally a protein, which is not analogous to a native gene product normally synthesized by that host animal cell. An "analogous" substance in this sense is a substance which performs substantially the same function in substantially the same way to produce substantially the same result.

Additionally, to achieve the objects and in accordance with the purposes of the present invention, two transhybridomas created by the above method are disclosed. These transhybridomas, A 15.9 and B 6.4 have been deposited in the Collection Nationale Des Cultures de Micro-Organismes (CNCM) under Accession Nos. I-535 and I-536, respectively.

To create the selectable transgenic host animal cells capable of producing gene products which are not analogous to gene products naturally produced by these cells, it has been found that the genetic material inserted into the embryo in creating the transgenic animal should contain not only a first DNA segment encoding the non-analogous gene product but also a second DNA segment capable of directing expression of the non-analogous gene product by the selected transgenic animal cell. Hereinafter, this second DNA segment is referred to as a promoter/enhancer element. In a preferred embodiment, the promoter/enhancer element and the first DNA segment (the encoding DNA sequence) are inserted into the fertilized egg of the host animal in a form known as a "fusion gene." The general procedure for the preparation of such fusion genes is well known to those of ordinary skill in the art, particularly in light of references such as Palmiter, Nature 300:611-615 (1982) and Ornitz et al., Nature 13:600 (1985), both of which are specifically incorporated herein by reference.

In the creation of the fusion gene, the selection of the second DNA segment, i.e., the DNA constituting the promoter/enhancer element, is of relative importance. The promoter/enhancer element which is chosen is to be capable of directing transcription and translation in the selected host animal cell. In a preferred embodiment, the promoter/enhancer element is selected from the group consisting of (1) the promoter of the H-2K gene; (2) the mouse metallothionein 1 promoter; and (3) any promoter/enhancer which is generally functional in normal or transformed (immortalized) lymphocytes. It should be noted that additional promoter/enhancer elements useful to create the products of the present invention may be selected by those of ordinary skill in the art in light of the teachings of the prior art, particularly in light of the teachings of Picard et al., Nature 307:80 (1984), specifically incorporated herein by reference, and the insights gained from the present specification.

Moreover, it is to be noted that the first DNA segment, which forms a part of the fusion gene discussed above, is selected from the entire body of DNA's, including cDNA's and genomic DNA's, which are known or which can be isolated or developed according to known methods by those of ordinary skill in the art. In certain embodiments, these DNA's are non-analogous in that the naturally-occuring genome of the proposed transgenic animal does not contain a contiguous section of DNA on a single chromosome which is identical to the first DNA segment. In a preferred embodiment, the first DNA segment is selected from the group of DNA's encoding human growth hormone. In a particularly preferred embodiment, the first DNA segment encodes human growth hormone.

In addition to the promoter/enhancer and the first DNA segment, the fusion gene may also contain a signal sequence, i.e., a DNA sequence encoding a signal peptide. This signal sequence would be useful in mediating the extracellular transport of the transgenic gene product. A preferred signal sequence is the DNA sequence encoding the immunoglobulin signal peptide.

The fusion gene, when obtained or created, is introduced into the genome host animal by micro-injection into the pronucleus of a host animal fertilized egg. The details of this procedure are set forth more fully in the examples which follow. Upon obtaining the resultant transgenic host animal, the now-transgenic host animal cells of interest may be harvested from the animal and maintained in culture by standard tissue culture methods.

While the tissue culture preparation obtained in this manner will express the non-analogous gene product encoded by the fusion gene, it has been recognized that there are certain disadvantages to the maintenance of non-immortalized cell lines for long periods of time in the laboratory. Thus, the present inventors have also developed a method for creating a "transhybridoma," i.e., a hybridoma in which one of the parent cell lines has been obtained from a transgenic animal. This method comprises:

(a) selecting a host animal from which a fertilized egg can be obtained;

(b) selecting a particular cell type of the host animal, which cell type is capable of being immortalized;

(c) constructing a fusion gene comprising promoter/enhancer elements competent in the selected host animal cell type and the DNA sequences encoding a desired gene product to be produced;

(d) introducing the fusion gene into a the host animal genome by micro-injection of the fusion gene into the pro-nucleus of a fertilized host animal egg;

(e) allowing the fertilized host animal egg containing the fusion gene to develop into a transgenic version of the host animal;

segregating the now-transgenic selected cells of the animal host which are producing the gene product from the transgenic animal;

(g) causing the now-transgenic selected cells to become immortalized to create a transhybridoma;

(h) culturing the transhybridoma; Moreover, this method may be used to produce the foreign gene product by the additional step of:

(i) harvesting the gene product of interest from the transhybridoma.

It is to be noted that, in this method for the creation of transhybridomas and gene products, the fusion gene may contain one or more DNA sequences encoding an analogous or a nonanalogous gene product. Thus, fusion genes suitable for use in this method include the fusion genes described above.

In this method, it is preferred that the cells obtained from the transgenic animal are selected from the group consisting of, for example, lymphocytes, fibroblasts and hepatocytes.

This method contemplates immortalizing cells either by fusion with an immortalized cell line or by immortalization by an agent such as a viral agent. In a particularly preferred embodiment, the transhybridomas of this method are created from the fusion of transgenic mouse lymphocytes containing and expressing the human growth hormone gene and a myeloma cell line X63-AG8-653, described by Kohler & Gilstein in Nature (1975), specifically incorporated herein by reference. However, transhybridomas may also be created by immortalization as a result of infection with a viral agent such as Epstein-Barr virus, retroviruses and the like.

The present inventors have developed two transhybridomas according to this method. The detailed protocols for the development of these hybridomas are described more fully in the Examples below. These transhybridomas have been designated A 15.9 and B 6.4 and have been deposited in the Collection Nationale Des Cultures de Micro-Organismes (CNCM) under Accession Nos. I-535 and I-536, respectively.

The present inventors contemplate various uses for the gene products described herein and created using the instant transhybridomas. Specifically, these gene products may be used as or incorporated into vaccines or used as diagnostic reagents in known biochemical and physiological assays and procedures. These gene products may also be used as or incorporated into therapeutic or pharmaceutical preparations.

It is understood that the application of the teachings of the present invention to a specific problem or environment will be within the capabilities of one having ordinary skill in the art in light of the teachings contained herein. Examples of the products of the present invention and representative processes for their isolation and manufacture appear in the following Examples.

EXAMPLE 1

Transgenic mice have been obtained after microinjection of a fusion gene consisting of 2kb of the 5' flanking sequence of the H-2k$^b$ gene, including its promoter, fused to the coding sequences of the hGH gene. This construction is illustrated in FIG. 1.

To create pH-2K$^b$ hGH, the 2.15Kb BamHI fragment, including the hGH structural gene, of the MThGH 111 plasmid as described by palmiter et al. in Science 222:809–814 (1983), specifically incorporated herein by reference, was inserted between the BqlII and BamHI sites of the pCα CAT vector. The pCα CAT vector has been described previously by Herbomel et al. in Cell 39:653–662 (1984), specifically incorporated herein by reference. A XhoI linker was then added at the single SalI site, resulting in the pBXGH plasmid.

The HindIII-NruI 2Kb fragment of the H-2K$^b$ promoter was subcloned at the HindIII site of the pSB1 plasmid also described by Herbomel et al., supra. The resulting plasmid was HindIII restricted and ligated to a XhoI linker. The XhoI-SalI fragment containing the H-2K$^b$ promoter was cut out and inserted into the pBXGH XhoI restricted plasmid, resulting into the pH-2K$^b$ hGH 6.6 kb plasmid. The thin lines depicted in FIG. 1 are pBR322 sequences; solid boxes are H-2K$^b$ promoter sequences and open boxes are hGH sequences. The position of transcriptional initiation from the H-2K$^b$ promoter as well as the ATG codon from the hGH genes are also indicated. The A and B PvuII fragments indicate the probes which have been used for the detection of transgenic mice.

The hGH structural gene was used as a marker gene because the presence of hGH DNA and mRNA could be assayed easily using a hGH specific probe. Moreover, if hGH mRNA was translated appropriately and the hormone secreted in the blood, increased growth should have been observed. Thus 2kb of the 5' flanking region (including promoter) of the H-2K$^b$ gene were joined to the structural gene of the hGH as described in FIG. 1. In this construction, the fusion occurs in exon 1, retaining the translation initiation codon of the hGH gene and the 5' regulatory region of the H-2K$^b$ gene.

The resulting pH-2K hGH plasmid was doubly digested by XhoI and BamHI and approximately 500 copies were microinjected into the male pronucleus of (C57/SJ) F$_2$ eggs. The eggs were subsequently transferred into the oviducts of pseudopregnant receiptents as described by Palmiter et al., supra. Four hundred twenty-five eggs were injected, 327 (77%) survived and were reimplanted in 23 foster mothers. Twelve were gravid and had 45 pups of which 43 (13% of eggs surviving injection) survived to adulthood.

The circulating hGH levels of 42 animals was measured by a specific radioimmunoassay and ranged from undetectable (approximately 2ng) to 150 ug/ml. compared to normal values of 10 to 100 ng of mouse GH per ml as set forth in Table 1. Retention of the hGH sequences was scored by tail blots with an hGH specific probe (fragment B depicted in FIG. 1) that spans most of the hGH structural gene.

TABLE 1

| ANIMAL FO H-2K GH | SEX | GENE COPY nb PER CELL | SERUM GH (ng ml$^{-1}$) | RELATIVE GROWTH |
|---|---|---|---|---|
| 7 | m | 1 | 400 | 1.74 |
| 10 | f | 2 | 4000 | 2.14 |
| 12 | m | 12 | 40 | 1.09 |
| 15 | m | 10 | 4000 | 2.19 |
| 16 | m | 3 | 250 | 1.57 |
| 22 | m | 1 | 60 | 1.34 |
| 32 | f | 60 | 40 | 1.25 |
| 33 | f | 4 | 965 | 2 |
| 34 | f | 45 | 12 | 1.1 |
| 35 | f | 2 | 4000 | 2.37 |
| 36 | m | 16 | 150000 | 1.9 |
| 40 | m | 1 | 4000 | 1.9 |
| 42 | m | 1 | 8 | 1.06 |

A total of 13 animals out of 42 (+%) were positive for hGH DNA with a copy number ranging from 1 to 60 copies (see Table 1). All of them except two, transmitted, either naturally or after in vitro fertilization rescue, the integrated DNA to their offspring. Nine out of these 13 mice grew larger than their normal littermate and 6 out of them grew up to twice as large as controls. As already observed, the increased growth rate commenced at about 3 weeks but did not always plateau at twelve weeks of age: at least one animal (Of H-2K GH15) continued to grow (90g at eleven month of age). There was no correlation between weight gain and H-2K hGH gene dosage as the majority of the largest animals had only a few copies, and one of the three transgenic animals that did not grow larger had more than 40.

The levels of hGH and H-2 mRNAs were determined in a variety of tissues from giant F1 offspring by Northern blot analysis, using either the PvuII-PvuII 1050 bp long fragment as the hGH probe (see FIG. 1. fragment B) or the SmaI H-2K$^b$ single stranded DNA as the H-2 probe.

The hGH probe detected a 0.9 Kb long RNA in organs of giant transgenic mice. No hGH mRNA was detected in either liver, spleen or kidney of the F1 H-2K GH 34 which expressed very low level of hGH in blood. The steady state concentration of H-2 mRNA varied considerably from tissue to tissue, suggesting a differential regulation between organs; the same situation was observed for hGH mRNA.

However, as H-2 genes belong to a multigenic family in which not only the nucleotide sequences but also the length of the transcripts are very similar, the results of Northern analysis using H-2 probe could only give a crude estimate of H-2K mRNA steady state level among different organs. S1 mapping analysis of mRNA enables H-2K transcripts to be distinguished from other H-2 mRNAs. Such an experiment has been performed using 10 ug of RNA extracted from different organs of the F1 H-2K GH 36.18 giant mouse and of the F1 36.16 control littermate; RNA were hybridized to a single stranded DNA probe which, after S1 nuclease digestion, is protected by the second exon of H-2Kb mRNA. The relative steady state levels of H-2Kb mRNA in different organs of the two mice can be estimated by comparing the intensity of the two protected around 270 base bands in each sample with the same bands in the liver RNA, arbitrarily expressed as 1, by densitometric autoradiogram scanning. The results are reported in Table 2. These values indicate that (1) there is a hierarchy of H-2K$^b$ mRNA steady-state levels in different tissues, maximal expression being observed in the mesenteric lymph nodes and the lowest expression in the brain representing around 1% of the level found in the liver; (2) that this hierarchy is very similar from one animal to the other; and (3) that production of high level of hGH mRNA in F1 H-2K GH 36.18 does not alter endogeneous H-2K gene expression.

TABLE 2

|  | H-2k mRNA | | hGH mRNA | |
|---|---|---|---|---|
|  | Fl 36 18 | Fl 36 16 | Fl 36 18 | Fl 7.3 |
| M.L.N. | 1 | 1.5 | 1.3 | n.t |
| LIVER | 1 | 1 | 0.4 | 1 |
| SPLEEN | 0.8 | 0.9 | 1 | 1.1 |
| THYMUS | 0.3 | 0.4 | 0.3 | 0.4 |
| KIDNEY | 0.25 | 0.25 | 0.90 | 0.20 |
| HEART | 0.20 | 0.25 | 0.45 | 0.10 |
| MUSCLE | 0.10 | 0.10 | n.t. | 0.12 |
| BRAIN | 0.01 | 0.01 | 0.01 | 0.01 |

If the H-2K hGH fusion gene is regulated properly, the pattern of hGH mRNA expression should mimic that of the H-2K mRNA. Certain tests, where levels of RNA in different organs of the F1 H-2K GH 36.18(A) and of the F1 H-2K GH 7.3(B) giant mice were determined by hybridization with the probe 2, which protects the second exon of hGH after S1 treatment, indicate that hGH mRNA is detected in all organs and that the hierarchy of expression observed is similar to that obtained for endogeneous H-2K$^b$ gene expression: maximal expression is found in the lymphoid organs and the lowest in the brain (see Table 2). However, although mouse F1 H-2K hGH 7.3 follows this hierarchy for all the organs, one can observe 2 main variations in the F1 H-2K hGH 36.18 organs: a lower production of hGH mRNA in the liver, and an over production in the kidney.

To confirm that the transcription of the hGH gene initiates in the H-2 promoter, an S1 mapping experiment was undertaken using a probe which covers the junction between H-2K and hGH. If H-2K hGH transcripts are properly initiated in the H-2K$^b$ promoter, a protected fragment of 93 nucleotides should be obtained. Such a fragment was found in 3 tested organs of a giant transgenic mouse: mesenteric lymph, spleen and liver RNA.

EXAMPLE 2

Using the method of Example 1, transgenic mice were created. The spleen of one animal, F1 H-2K hGH 36, was used to produce hybridomas by fusion with the X63 - Ag 8 - 653 myeloma described by Kohler et al. in Nature 256:495-497 (1975), specifically in-corporated herein by reference.

Thirty-six independent clones were scored for hGH production in the supernatant; all of them were found to be positive, with 13 producing from 3 to 10 ng/ml, 18 producing from 10 to 40 ng/ml, and 5 producing from 40 to 160 ng/ml as set forth in Table 3. The variation observed between different clones was similar to that observed normally when measurements of the amounts of monoclonal antibodies synthesized by classical hybridomas are made.

TABLE 3

| Production Of hGH By Transhybridomas And Derived Ascites | | | | | |
|---|---|---|---|---|---|
| A | | B | | C | |
| Hybridomas | ng/ml | subclones | ng/ml | ascite fluid | ng/ml |
| A1 | 3.7 | | | | |

TABLE 3-continued

Production Of hGH By Transhybridomas And Derived Ascites

| A Hybridomas | ng/ml | B subclones | ng/ml | C ascite fluid | ng/ml |
|---|---|---|---|---|---|
| A6 | 8.4 | | | | |
| A17 | 7.4 | | | | |
| | | A15.9 | 148 | A15.9 | 15,200 |
| A9 | 11.2 | A15.10 | 76 | A15.10 | 10,000 |
| A14 | 30 | | | | |
| B9 | 19.8 | | | | |
| B10 | 20.9 | B6.4 | 158 | B6.4 | 21,200 |
| A8 | 40.3 | B6.6 | 69 | B6.6 | 4,500 |
| A13 | 56 | | | | |
| A15 | 73 | | | | |
| B6 | 120 | | | | |
| B12 | 60.6 | | | | |

After subcloning, two of the hybridomas producing the largest amounts of hGH in their supernatant (160 ng/ml for clone B6-4 and 76 ng/ml for clone A15-10) were used to induce ascites in nude mice. Three weeks after intraperitoneal injection of cells, ascitic fluid was collected and centrifuged and the amount of hGH in the supernatant was measured by radioimmunoassay. Twenty-one micrograms of hGH were produced per milliliter of ascitic fluid in the case of B6-4 and 10 ug in the case of A15-10. The biological activity of the hormone has not been measured: it is nevertheless highly probable that the molecule is biologically active as it has been produced by cells taken from animal which indeed was giant, and thus must have produced an active hormone.

EXAMPLE 3

Thus, it has been shown that lymphocytes bearing a fusion gene with a promoter functional in these cells may be immortalized through fusion with a myeloma and produce the protein encoded in the fusion gene. This approach may be extended to any other secreted protein which is made in minute amounts.

Several improvements and generalizations are envisaged: firstly the promoter/regulator sequences of the immunoglobulin heavy (IgH) - chain gene as described by Banerji et al. in Cell 33:729-740 (1983) and Neuberger in EMBO J. 2:1373-1378 (1984), both of which are specifically incorporated herein by reference, are to be investigated. Secondly, the possibility of producing in the same way proteins which are normally not secreted is to be explored by including in the fusion gene sequences coding for a signal peptide.

It will be apparent to those skilled in the art that various modifications and variations can be made to the processes and products of the present invention. Thus, it is intended that the present invention cover these modifications and variations of this invention provided they come within the scope of the appended claims and their equivalents.

What is claimed is:
1. An immortalized transgenic eukaryotic cell A 15.9.
2. An immortalized transgenic eukaryotic cell B 6.4.

* * * * *